United States Patent [19]

Gohzu et al.

[11] Patent Number: 5,013,445

[45] Date of Patent: May 7, 1991

[54] METHOD FOR SEPARATING IMMUNOGLOBULIN G. SUBCLASSES

[75] Inventors: Shunichi Gohzu; Misao Horie, both of Yokohama; Kuniyo Inouye, Sagamihara, all of Japan

[73] Assignee: Tosoh Corporation, Shinnanyo, Japan

[21] Appl. No.: 511,978

[22] Filed: Apr. 16, 1990

Related U.S. Application Data

[63] Continuation of Ser. No. 219,434, Jul. 15, 1988, abandoned.

[30] Foreign Application Priority Data

Jul. 15, 1987 [JP] Japan ................. 62-174763

[51] Int. Cl.$^5$ ............................. B01D 15/08
[52] U.S. Cl. ..................... 210/635; 210/656; 530/387; 530/417
[58] Field of Search ............. 530/387, 417; 210/635, 210/656, 198.2

[56] References Cited

U.S. PATENT DOCUMENTS

| | | | |
|---|---|---|---|
| Re. 27,806 | 10/1973 | Dienst | 530/417 |
| 3,487,064 | 12/1969 | Swanson | 530/417 |
| 3,857,829 | 12/1974 | Smithwick | 530/417 |
| 4,136,094 | 1/1979 | Condie | 530/387 |
| 4,421,684 | 12/1983 | Nakashima | 530/387 |
| 4,469,630 | 9/1984 | Flashner | 530/417 |
| 4,490,290 | 12/1984 | Gani | 210/679 |
| 4,511,502 | 4/1985 | Builder | 530/417 |
| 4,512,897 | 4/1985 | Crowder | 210/656 |
| 4,537,712 | 8/1985 | Oh | 530/417 |
| 4,604,235 | 8/1986 | Flashner | 530/417 |
| 4,606,825 | 8/1986 | Crane | 210/656 |
| 4,639,513 | 1/1987 | Hou | 530/387 |
| 4,704,366 | 11/1987 | Salinas | 530/387 |

FOREIGN PATENT DOCUMENTS 144028  6/1985  European Pat. Off. ......... 210/198.2

OTHER PUBLICATIONS

Mikes Laboratory Handbook of Chromatographic and Allied Methods, Ellis Horwood, John Wileys and Sons, New York, 1979.
Chemical Abstracts, vol. 100, #101314u (1984).
J. of Immunological Methods, vol. 80, pp. 89-98 (1985), "Purification of In Vitro Produced Mouse Monoclonal Antibodies".
"Molecular Immunology", Marcel Dekker, N.Y. (1984), pp. 288 and 293.
Chemical Abstracts, vol. 105, #224026u (1986).

Primary Examiner—Ernest G. Therkorn
Attorney, Agent, or Firm—Oblon, Spivak, McClelland, Maier & Neustadt

[57] ABSTRACT

A method for separating immunoglobulin G subclasses, which comprises separating immunoglobulin G subclasses by liquid chromatography by using as the solid phase a porous gel having an exclusion limit molecular weight larger than the molecular weight of immunoglobulin G, as calculated as protein, and a buffer solution having an ionic strength of from 0.1 to 2.0M.

8 Claims, No Drawings

METHOD FOR SEPARATING IMMUNOGLOBULIN G. SUBCLASSES

This application is a continuation of application Ser. No. 07/219,434, filed on July 15, 1988, now abandoned.

BACKGROUND OF THE INVENTION

1. Field of the Invention

The present invention relates to a method for separating immunoglobulin G subclasses. More particularly, it relates to a method for separating immunoglobulin G subclasses with high efficiency and precision.

2. Discussion of the Background

Immunoglobulin G (hereinafter referred to simply as IgG) has a structural unit comprising pairs of identical heavy chains (H-chains) and light chains (L-chains) linked by disulfide bonds (S—S bonds) as the basic structure in the same manner as other immunoglobulins. It is further classified into a plurality of subclasses based on the types of H-chains. For example, human IgG is classified into subclasses IgG 1, IgG 2, IgG 3 and IgG 4 having H-chains of different structures such as $\gamma$-1, $\gamma$-2, $\gamma$-3 and $\gamma$-4, respectively. Likewise, mouse IgG is classified into subclasses IgG 1, IgG 2a, IgG 2b and IgG 3. Such IgG subclasses have different physiological activities against complements or against phagocytes, but their properties such as the molecular weights and stereostructures are similar to one another. Therefore, as a method for separating such subclasses, it has been common to employ a separation method by affinity chromatography utilizing the differences in the affinity to protein A produced by Staphylococcus. The molecular weight of IgG is said to be about 150,000.

However, such a method of separating subclasses by affinity chromatography by means of protein A has problems such that it is necessary to change the pH of the fluent and the operation is therefore cumbersome and time-consuming, IgG 3 does not bind to protein A, and the separation of subclasses is inadequate.

SUMMARY OF THE INVENTION

The present inventors have conducted extensive research to solve these problems and as a result, have found it possible to solve these problems by utilizing discreet or subtle differences in e.g. the hydrophobic bonding of the gel and the IgG subclasses in liquid chromatography. The present invention has been accomplished on the basis of this discovery.

The present invention provides a method for separating immunoglobulin G subclasses, which comprises separating immunoglobulin G subclasses by liquid chromatography by using as the solid phase a porous gel having an exclusion limit molecular weight larger than the molecular weight of immunoglobulin G, as calculated as protein, and a buffer solution having an ionic strength of from 0.1 to 2.0 M.

DETAILED DESCRIPTION OF THE PREFERRED EMBODIMENTS

Now, the present invention will be described in detail with reference to the preferred embodiments.

The present invention is designed to separate IgG subclasses based on the differences in the mobility of the subclasses in the solid phase attributable to the differences in the interaction such as the hydrophobic bonding with the gel due to discreet differences in e.g. the composition of amino acids in the $\gamma$-chains determining the respective subclasses.

The gel used as the solid phase in the present invention may be any porous gel having an exclusion limit molecular weight larger than the molecular weight of IgG as calculated as protein. For example, it may be made of an inorganic gel such as glass or silica, a polymer gel such as styrene, ethylene glycol or methacrylate gel, or copolymer thereof, or a polysaccharide such as dextrane, agalose or starch. Preferred is an inorganic gel such as silica, particularly a hydrophilic gel having an average particle size of at most 50 $\mu$m and a plurality of hydrophilic groups such as hydroxyl groups and being capable of preventing the adsorption of IgG to the gel. More preferably, a fine particle gel having an average particle size of about 10 $\mu$m may be employed. By using such a gel, the precision in the separation of IgG subclasses is improved. However, in order to obtain a suitable flow rate, it may be necessary to conduct the separation under a pressurized condition. In such a case, the gel must have an adequate pressure resistance.

The buffer solution used as the mobile phase may be a usual buffer solution having a pH of from 3.0 to 10.0. For example, a buffer solution of e.g. boric acid, phosphoric acid, citric acid, carbonic acid or a salt thereof, or trishydroxymethylaminomethane. It is preferably a 5-100 mM phosphoric acid or trishydroxymethylaminomethane buffer solution adjusted to have a pH of from 6.0 to 7.5, which is capable of preventing ionic adsorption of IgG subclasses to the gel and which does not adversely affect the activities of IgG subclasses after separation.

The ionic strength of the buffer solution in the present invention is adjusted within a range of from 0.1 to 2.0M, preferably from 0.1 to 1.0M, by adding an inorganic salt commonly employed in a biochemical technique, for example, an alkali metal or alkaline earth metal halide such as NaCl, KCl or $CaCl_2$, to control the hydrogen bonding of the gel and the IgG subclasses and to separate the subclasses by utilizing the discreet differences in the interaction such as the hydrophobic bonding with the gel, which are attributable to the differences in the composition of amino acids among the subclasses. The addition of such an inorganic salt may be made as the case requires in order to adjust the ionic strength of the buffer solution to the above-mentioned range. If the ionic strength of the buffer solution is less than 0.1M, the separation of subclasses tends to be difficult due to the hydrogen bonding between the gel and IgG subclasses. On the other hand, if the ionic strength is more than 2.0 M, the eluted peak of each subclass tends to be blunt, whereby the separation will be poor.

Samples containing IgG subclasses include bloods and body fluids of animals such as blood serum, antiserum, IgG polyclonal antibody or IgG monoclonal antibody. In the case of a sample containing many components other than IgG subclasses, such as blood serum, it is advisable to conduct purification for IgG by a usual method such as salting out or size exclusion chromatography, prior to the separation of the IgG subclasses.

In the present invention, it is unnecessary to change the pH of the eluent during the elution as is required for the separation method of IgG subclasses by affinity chromatography by means of protein A. Therefore, the present invention has a significant feature that the separation of IgG subclasses can be conducted efficiently in a simple operation without adversely affecting the physiological activities of IgG subclasses. Further, the present invention is applicable for the separation of an IgG sample, the physiological activities of which have decreased and which can not be separated by affinity chromatography since the affinity to protein A has decreased.

Now, the present invention will be described with reference to Examples. However, it should be understood that the present invention is by no means restricted to such specific Examples.

EXAMPLE 1

A commercially available monoclonal antibody-containing sample which contained 30 ml of each of mouse IgG subclasses (IgG 1, IgG 2a, IgG 2b, IgG 3:1 mg/ml), was subjected to liquid chromatography (HLC® 8020, tradename, manufactured by TOSOH CORPORATION) by using as the solid phase a hydrophilic silica gel (TSK-gel G 3000SW, tradename, manufactured by TOSOH CORPORATION) having an exclusion limit molecular weight of 50,000 (as calculated as protein) and as the mobile phase a 0.1M phosphate buffer solution (pH 7.0) containing 0.05M NaCl. The ionic strength of the mobile phase was 0.24M. The flow rate of the mobile phase was 1.0 ml/min, and the elution of IgG subclasses were observed by measuring the changes in the absorbance at 280 nm. Eluted IgG subclasses were identified by Ouchterlony reaction.

The elution time of the respective IgG subclasses was as follows:

IgG 1:15.13, IgG 2a:14.34, IgG 2b:13.35, IgG 3: 17.0 (min).

EXAMPLE 2

The separation of the IgG subclasses were conducted in the same manner as in Example 1 except that a 0.1M phosphate buffer solution (pH 7.0) containing 0.8M NaCl was used as the mobile phase. The ionic strength of the mobile phase was 0.99M. The elution time of the respective subclasses was as follows:

IgG 1:15.21, IgG 2a:14.36, IgG 2b:13.49, IgG 3: 17.11 (min).

Obviously, numerous modifications and variations of the present invention are possible in light of the above teachings. It is therefore to be understood that within the scope of the appended claims, the invention may be practiced otherwise than as specifically described herein.

What is claimed is:

1. A method for separating immunoglobulin G subclasses, which comprises separating immunoglobulin G subclasses by liquid chromatography by using as the solid phase a porous gel having an exclusion limit molecular weight larger than the molecular weight of immunoglobulin G, as calculated as protein, and a buffer solution having an ionic strength of from 0.1 to 2.0M, to obtain said immunoglobulin G subclasses in substantially isolated form, wherein said chromatography is carried out without adjusting the pH of said buffer solution.

2. The method according to claim 1, wherein the porous gel is an inorganic gel, a polymer gel, a copolymer gel or a polysaccharide gel.

3. The method according to claim 1, wherein the porous gel is an inorganic gel having an average particle size of at most 50 μm.

4. The method according to claim 3, wherein the inorganic gel is silica.

5. The method according to claim 1, wherein the buffer solution has a pH of from 3.0 to 10.0.

6. The method according to claim 1, wherein the buffer solution is a 5–100 mM phosphoric acid or trishydroxymethylaminomethane buffer solution having a pH of from 6.0 to 7.5.

7. The method according to claim 1, wherein the ionic strength of the buffer solution is from 0.1 to 1.0M.

8. A method for separating immunoglobulin G subclasses, which comprises separating immunoglobulin G subclasses by liquid chromatography by using as the solid phase a hydrophilic porous gel having an exclusion limit molecular weight of 50,000, as calculated as protein, and a phosphate buffer solution having an ionic strength of from 0.24 to 0.99, and containing from 0.05M NaCl to 0.8M NaCl, as the mobile phase, to obtain said immunoglobulin G subclasses in substantially isolated form, wherein said chromatography is carried out without adjusting the pH of said phosphate buffer solution.

* * * * *